United States Patent [19]
Fischetti et al.

[11] Patent Number: 5,985,654
[45] Date of Patent: Nov. 16, 1999

[54] RECOMBINANT POXVIRUS AND STREPTOCOCCAL M PROTEIN VACCINE

[75] Inventors: Vincent A. Fischetti, West Hempstead, N.Y.; Dennis E. Hruby, Corvallis, Oreg.

[73] Assignees: The Rockefeller University, Corvallis, Oreg.; Oregon State University, New York, N.Y.

[21] Appl. No.: 08/205,348

[22] Filed: Mar. 3, 1994

Related U.S. Application Data

[63] Continuation of application No. 08/089,415, Jul. 9, 1993, abandoned, which is a continuation of application No. 07/962,048, Oct. 16, 1992, abandoned, which is a continuation of application No. 07/540,586, Jun. 19, 1990, abandoned, which is a continuation-in-part of application No. 07/369,118, Jun. 21, 1989, abandoned.

[51] Int. Cl.⁶ .................................................. C12N 15/63
[52] U.S. Cl. ...................... 435/320.1; 435/885; 530/324; 530/325; 530/326; 530/327; 530/328; 530/350; 930/10; 930/200; 935/1; 935/11; 935/12; 935/22; 935/32; 536/23.1; 536/23.7

[58] Field of Search .................................. 435/69.1, 69.3, 435/235.1, 317.1, 320.1, 885; 530/336, 324–328, 350; 536/23.1, 23.2, 23.4, 23.5, 23.51, 23.52, 23.7; 930/10, 20, 200; 514/12, 13, 14, 88; 935/1, 11, 12, 22, 32

[56] References Cited

PUBLICATIONS

Hruby et al. (Aug., 1988), PNAS, vol. 85, pp. 5714–5717.
Hollingshead et al. (1986), The Journal of Biological Chemistry vol. 261, No. 4, pp. 1677–1686.
Rice et al. (1985), Journal of Virology, vol. 56, No. 1 pp. 227–239.
Taylor et al. (Dec. 1988) Vaccine, vol. 6, pp. 497–503.

*Primary Examiner*—Jeffrey Stucker
*Attorney, Agent, or Firm*—Burns, Doane, Swecker & Mathis, L.L.P.

[57] ABSTRACT

Viruses of the family poxviridae such as vaccinia or fowlpox viruses are modified to contain a gene which expresses a protein corresponding to the conserved exposed region of the M6 protein. The modified products are useful as vaccines against streptococcal infection.

11 Claims, 6 Drawing Sheets

|     | a   | b   | c   | d   | e   | f   | g   |
|-----|-----|-----|-----|-----|-----|-----|-----|
|     | Arg | Val | Phe | Pro | Arg | Gly | Thr |
|     | Val | Glu | Asn | Pro |     |     |     |
| 12  |     | Asp | Lys | Ala | Arg | Glu | Leu |
| 18  | Leu | Asn | Lys | Tyr | Asp | Val | Glu |
| 25  | Asn | Ser | Met | Leu | Gln | Ala | Asn |
| 32  | Asn | Asp | Lys | Leu | Thr | Thr | Glu |
| 39  | Asn | Asn | Asn | Leu | Thr | Asp | Glu |
| 46  | Asn | Lys | Asn | Leu | Thr | Thr | Glu |
| 53  | Asn | Lys | Asn | Leu | Thr | Asp | Glu |
| 60  | Asn | Lys | Asn | Leu | Thr | Thr | Glu |
| 67  | Asn | Lys | Asn | Leu | Thr | Asp | Gln |
| 74  | Asn | Lys | Asn | Leu | Thr | Thr | Glu |
| 81  | Asn | Lys | Glu | Leu | Lys | Ala | Glu |
| 88  | Glu | Asn | Arg | Leu | Thr | Thr | Glu |
| 95  | Asn | Lys | Gly | Leu | Thr | Lys | Lys |
| 102 | Leu | Ser | Glu | Ala | Glu | Glu | Glu |
| 109 | Ala |     |     |     |     |     |     |
| 110 | Ala | Asn | Lys | Glu | Arg | Glu | Asn |
| 117 | Lys | Glu | Ala | Ile | Gly | Thr | Leu |
| 124 | Lys | Lys | Thr | Leu | Asp | Glu | Thr |
| 131 |     |     |     | Val | Lys | Asp | Lys |
| 135 | Ile | Ala | Lys | Glu | Gln | Glu | Ser |
| 142 | Lys | Glu | Thr | Ile | Gly | Thr | Leu |
| 149 | Lys | Lys | Thr | Leu | Asp | Glu | Thr |
| 156 |     |     |     | Val | Lys | Asp | Lys |
| 160 | Ile | Ala | Lys | Glu | Glu | Glu | Ser |
| 167 | Lys | Glu | Thr | Ile | Gly | Thr | Leu |
| 174 | Lys | Lys | Thr | Leu | Asp | Glu | Thr |
| 181 |     |     |     | Val | Lys | Asp | Lys |
| 185 | Ile | Ala | Lys | Glu | Gln | Glu | Ser |
| 192 | Lys | Glu | Thr | Ile | Gly | Thr | Leu |
| 199 | Lys | Lys | Ile | Leu | Asp | Glu | Thr |
| 206 |     |     |     | Val | Lys | Asp | Lys |
| 210 | Ile | Ala | Arg | Glu | Glu | Lys | Ser |
| 217 | Lys | Gln | Asp | Ile | Gly | Ala | Leu |
| 224 | Lys | Gln | Glu | Leu | Ala | Lys | Lys |
| 231 |     |     |     |     | Asp | Glu | Gly |
| 234 | Asn | Lys | Val | Ser | Glu | Ala | Ser |
| 241 | Arg | Lys | Gly | Leu | Arg | Arg | Asp |
| 248 | Leu | Asp | Ala | Ser | Arg | Glu | Ala |
| 255 | Lys | Lys | Gln | Val | Glu | Lys | Asp |
| 262 | Leu | Ala | Asn | Lue | Thr | Ala | Glu |
| 269 | Leu | Asp | Lys | Val | Lys | Glu | Glu |
| 276 | Lys | Gln | Ile | Ser | Asp | Ala | Ser |
| 283 | Arg | Gln | Gly | Leu | Arg | Arg | Asp |
| 290 | Leu | Asp | Ala | Ser | Arg | Glu | Ala |
| 297 | Lys | Lys | Gln | Val | Glu | Lys | Ala |
| 304 | Leu | Glu | Glu | Ala | Asn | Ser | Lys |
| 311 | Leu | Ala | Ala | Leu | Glu | Lys | Leu |
| 318 | Asn | Lys | Glu | Leu | Glu | Glu | Ser |
| 325 | Lys | Lys | Leu | Thr | Glu | Lys | Glu |
| 332 | Lys | Ala | Glu | Leu | Gln |     |     |
| 337 |     | Ala | Lys | Leu | Glu | Ala | Glu |
| 343 | Ala | Lys | Ala | Leu | Lys | Glu | Gln |
| 350 | Leu | Ala | Lys | Gln | Ala | Glu | Glu |
| 357 | Leu | Ala | Lys | Leu | Arg | Ala |     |
| 363 | Gly | Lys | Ala | Ser | Asp | Ser | Gln | Thr |
| 371 | Pro | Asp | Ala | Lys |     |     |     |
| 375 | Pro | Gly | Ala | Lys | Val | Val |     |
| 381 | Pro | Gly | Lys | Gly | Gln | Ala |     |
| 387 | Pro | Gln | Ala | Gly | The | Lys |     |
| 393 | Pro | Asn | Gln | Asn | Lys | Ala |     |
| 399 | Pro | Met | Lys | Glu | Thr | Lys | Arg | Gln | Leu |
| 408 | Pro | Ser | Thr | Gly | Glu | THr | Ala | Asn | Pro |
| 417 | Phe | Phe | Thr | Ala | Ala | Ala | Leu |
| 424 | Thr | Val | Met | Ala | Thr | Ala | Gly |
| 431 | Val | Ala | Ala | Val | Val |     |     |
| 436 | Lys | Arg | Lys | Glu | Glu | Asn |     |

AMINO ACID SEQUENCE OF
THE M6' PROTEIN

FIG. 5

MKIAREQKSKQDIGALKQELAKKDEGNKVSEASRKGLRRDLDA
SREAKKQVEKDLANLTAELDKVKEEKQISDASRQGLRRDLDAS
REAKKQVEKALEEANSKLAALEKLNKELEESKKLTEKEKAELQ
AKLEAEAKALKEQLAKQAEELAKLRAGKASDSQTPDAKPGNKV
VPGKGQAPQAGTKPNQNKAPMKETKRQLPSTGETANPFFTAAA
LTVMATAGVAAVVKRKEEN

FIG.4

```
AAGATGAAATT
GCGAGAGAGC  AAAAAAGTAA  ACAAGACATT  GGTGCCCTTA  AACAAGAATT  AGCTAAAAAA
GATGAAGGAA  ACAAAGTTTC  AGAAGCAAGC  CGTAAGGGTC  TTCGCCGTGA  CTTGGACGCA
TCACGTGAAG  CTAAGAAACA  GGTTGAAAAA  GATTTAGCAA  ACTTGACTGC  TGAACTTGAT
AAGGTTAAAG  AAGAAAAACA  AATCTCAGAC  GCAAGCCGTC  AAGGTCTTCG  CCGTGACTTG
GACGCATCAC  GTGAAGCTAA  GAAACAAGTT  GAAAAAGCTT  TAGAAGAAGC  AAACAGCAAA
TTAGCTGCTC  TTGAAAAACT  TAACAAGAG   CTTGAAGAAA  GCAAGAAATT  AACAGAAAAA
GAAAAGCTG   AGCTACAAGC  AAAACTTGAA  GCAGAAGCAA  AAGCACTCAA  AGAACAATTA
GCGAAACAAG  CTGAAGAACT  TGCAAAACTA  AGAGCTGGAA  AAGCATCAGA  CTCACAAACC
CCTGATGCAA  AACCAGGAAA  CAAAGTTGTT  CCAGGTAAAG  GTCAAGCACC  ACAAGCAGGT
ACAAACCTA   ACCAAAACAA  AGCACCAATG  AGGAAAACTA  AGAGACAGTT  ACCATCAACA
GGTGAAACAG  CTAACCCATT  CTTCACAGCG  GCAGCCCCTA  CTGTTATGGC  AACAGCTGGA
GTAGCAGCAG  TTGTAAAACG  CAAAGAAGAA  AAC
```

DNA SEQUENCE OF THE M6' GENE

RECOMBINANT POXVIRUS AND STREPTOCOCCAL M PROTEIN VACCINE

RELATED APPLICATIONS

This application is a continuation of U.S. application Ser. No. 08/089,415, filed Jul. 9, 1993, now abandoned, which is a continuation of U.S. application Ser. No. 07/962,048, filed Oct. 16, 1992, now abandoned, which is a continuation of U.S. application Ser. No. 07/540,586, filed Jun. 19, 1990, now abandoned, which is a continuation-in-part of U.S. application Ser. No. 07/369,118, filed Jun. 21, 1989, now abandoned.

This invention was made with government support under Grant Number AI-1182 awarded by the National Institutes of Health.

BACKGROUND OF THE INVENTION

This invention is concerned with viruses such as the vaccinia and fowlpox viruses modified to contain the DNA sequence (gene) which will express in a mammalian host, including humans, a protein corresponding to the conserved, exposed region of the M6 protein. It is concerned also with the use of such modified products as vaccines to protect against streptococcal infection. Further, it is concerned with plasmids or other vectors carrying the said gene.

Approximately 30 million cases of group A streptococcal infections occur each year in the United States, the most common of which is acute streptococcal pharyngitis which is found predominantly in school age children. Up to 5% of pharyngitis cases which have gone untreated, or have been ineffectively treated, can lead to acute rheumatic fever, a disease which can ultimately result in cardiac damage. While not a major problem in the United States, this streptococcal sequelae is a significant problem in developing nations of the world. For example, it has been estimated that nearly 6 million children of school age in India suffer from rheumatic heart disease.

The M protein of group A streptococci is a fibrous dimer of helices arranged in a coiled coil extending about 50 nm from the surface of these organisms. It is a fibrillar molecule of which there exists more than 80 serological types M. The protein renders the streptococcus resistant to nonimmune phagocytosis. It is the major virulence factor of streptococcal bacteria.

Thus, there are over 80 distinct serotypes of group A streptococci such that a vaccine based on type-specific epitopes may not be practical. In general, no satisfactory vaccine which will confer protection against streptococcal infection has yet been developed, although significant and costly efforts have been directed towards that end.

There is a strong impetus to develop a safe and effective vaccine against group A streptococci.

SUMMARY OF THE INVENTION

It has now been surprisingly found that a polypeptide corresponding to the C-terminal region of the M6 protein and encompassing the conserved exposed region of the M protein (herein sometimes referred to as the "M6' protein") can elicit a protective immune response when administered to a mammal. The M6' polypeptide can be produced by modifying the genome of a virus of the family poxviridae such as the orthopoxvirus vaccinia or the avipoxvirus fowlpox to contain a genetically engineered gene ("the M6' gene") which, expresses the M6' protein. The M6' protein can be administered to a mammal by administration to the mammal of a modified vaccinia or fowlpox virus containing a gene coding for the protein.

Thus, the present invention provides a protein capable of eliciting an immunoprotective response to streptococcal infection in a mammal, said protein comprises an amino acid sequence which is the same or substantially the same as the amino acid residue sequence in the conserved exposed region of the M6 protein. The present invention also provides the M6' protein.

Further, the present invention provides a gene coding for a protein capable of eliciting an immunoprotective response to a streptococcal infection in a mammal, wherein said protein comprises an amino acid sequence which is the same or substantially the same as an amino acid residue sequence in the conserved exposed region of the M6 protein. The present invention also provides the M6' gene.

In addition, the present invention provides a plasmid containing a gene coding for a protein capable of eliciting an immunoprotective response to streptococcal infection in a mammal, wherein said protein comprises an amino acid sequence which is the same or substantially the same as an amino acid residue sequence in the conserved exposed region of the M6 protein. The gene coding can be the M6' gene.

The present invention also provides a virus, preferably of the family poxviridae containing a gene coding for protein capable of eliciting an immunoprotective response to streptococcal infection in a mammal, wherein said protein comprises an amino acid sequence which is the same or substantially the same as an amino acid residue sequence in the conserved exposed region of the M6 protein. Typical poxviruses include vaccinia and fowlpox; fowlpox is a preferred virus. The gene the virus can contain is the M6' gene.

More generally, the present invention provides a virus containing a gene coding for a surface antigen or portion thereof of a prokaryote, said surface antigen or portion thereof being responsible for the virulence of said prokaryote. Typical viruses include those of the family poxviridae, especially vaccinia and fowlpox; fowlpox being a preferred virus. The surface antigen or portion thereof can be a protein capable of eliciting an immunoprotective response in a mammal, which comprises an amino acid sequence which is the same or substantially the same as an amino acid residue sequence in the conserved exposed region of the M6 protein. The prokaryote can be a bacteria, especially streptococcus. The gene the virus can contain is the M6' gene.

Likewise, the present invention provides a vaccine comprising a pharmaceutically acceptable carrier and a virus containing a gene coding for a surface antigen or portion thereof of a prokaryote, said surface antigen or portion thereof being responsible for the virulence of said prokaryote; and, said virus is present in a sufficient amount for sufficient antigen or portion thereof to elicit a protective response to an infection caused by said prokaryote. The surface antigen or portion thereof can be a protein capable of eliciting an immunoprotective response to streptococcal infection in a mammal, which comprises an amino acid sequence which is the same or substantially the same as an amino acid residue sequence in the conserved exposed region of the M6 protein; and the virus is present in a sufficient amount for sufficient protein to elicit a protective response to a streptococcal infection. The prokaryote can be a bacteria, especially streptococcus. Again, typical viruses include those of the family poxviridae, especially vaccinia and fowlpox; fowlpox is preferred; and, the gene the virus can contain is the M6' gene.

Furthermore, the present invention provides a method of controlling prokaryotic infection in a mammal in need of such control which comprises administration to said mammal of a virus containing a gene coding for a surface antigen or portion thereof of a prokaryote, said surface antigen or portion thereof being responsible for the virulence of said prokaryote; and said virus being administered in a sufficient amount for sufficient antigen or portion thereof to elicit an antibody response to an infection caused by said prokaryote. The surface antigen or portion thereof can be a protein capable of eliciting an immunoprotective response to streptococcal infection in a mammal, which comprises an amino acid sequence which is the same or substantially the same as an amino acid sequence in the conserved exposed region of the M6 protein; the virus being administered in a sufficient amount for the protein to elicit an antibody response sufficient to effect such control. The prokaryote can be a bacteria, especially streptococcus. Again, typical viruses include those of the family poxviridae, especially vaccinia and fowlpox; fowlpox is preferred; and the gene the virus can contain is the M6' gene.

The present invention additionally provides a gene coding for a segment of a surface antigen or portion thereof of a prokaryote, said surface antigen being responsible for the virulence of said prokaryote; and, said segment of surface antigen or portion thereof is capable of eliciting an immunoprotective response to infection caused by said prokaryote in a mammal. This is not a product of nature as the coding is for a segment of a surface antigen or portion thereof and not for the entire antigen.

The present invention likewise provides a plasmid containing a gene coding for a segment of a surface antigen or portion thereof of a prokaryote, said surface antigen being responsible for the virulence of said prokaryote; and, said gene coding not naturally being present in said plasmid.

The phrase "said gene coding not naturally being present in said plasmid" is employed so that it is clear that a product of nature is not being included within the scope of this invention. For instance, the novel M6' gene of this invention in the novel plasmid pVV3:M6' has been deposited at the American Type Culture Collection. The deposit was of a sample of the pVV3:M6' plasmid in E. coli under the accession number 68003. The M6' gene is not naturally present in a plasmid of E. coli; or, "said gene coding (the M6' gene) not naturally being present in said plasmid (of E. coli)." Likewise the term "segment of surface antigen or portion thereof" is employed so that the genes and plasmids within the scope hereof do not include products of nature or that which is already known, e.g., the M6 gene or the plasmid pVV3:M6.

Likewise, the present invention provides a vaccine comprising a pharmaceutically acceptable carrier and a virus, preferably of the family poxviridae containing a gene coding for protein capable of eliciting an immunoprotective response to streptococcal infection in a mammal, wherein said protein comprises an amino acid sequence which is the same or substantially the same as an amino acid residue sequence in the conserved exposed region of the M6 protein; and said virus is present in a sufficient amount for sufficient protein to elicit a protective response to a streptococcal infection. Again, typical poxviruses include vaccinia and fowlpox; fowlpox is preferred; and, the gene the virus can contain is the M6' gene.

The present invention additionally provides a method of controlling streptococcal infection in a mammal in need of such control which comprises administration to said mammal of a virus of the family poxviridae containing a gene coding for protein capable of eliciting an immunoprotective response to streptococcal infection in a mammal, wherein said protein comprises an amino acid sequence which is the same or substantially the same as the amino acid residue sequence in the conserved exposed region of the M6 protein; said virus being administered in a sufficient amount for the protein to elicit an antibody response sufficient to effect such control. Again, typical poxviruses include vaccinia and fowlpox; fowlpox is preferred; and the gene the virus can contain is the M6' gene.

The term "the same or substantially the same" is used herein to describe the sequence of amino acids in proteins of this invention having the desirable activity because such proteins are either identical to the exposed conserved region of the M6 protein of a group A streptococci or so similar to the segment that they have the same activity. No undue experimentation is required to determine proteins which are so similar to the conserved exposed region of the M6 protein that they have the same activity as those which are the same as the region. The skilled artisan, from reading this specification can prepare homologous polypeptides having the same activity and substantially the same sequence as the exposed conserved region of the M6 protein. For instance, the termini may be extended, e.g., to provide an anchor to bind the protein to a binder. A protein with the same activity and a high degree of homology with the conserved exposed region might be synthesized more readily or be less expensive to prepare, and, this protein is considered within the scope of this invention.

To clarify the terms used herein still further, the proteins of the present invention are not the entire M protein, but rather, have the same, or substantially the same amino acid sequence as the conserved, exposed region of the M6 protein of group A streptococci (or a portion thereof). The polypeptides of this invention are not considered to be naturally occurring. To obtain the proteins of this invention, viruses are genetically modified to express these proteins. However, having disclosed herein the conserved, exposed region of the M6 protein of group A streptococci and the utility thereof, synthesis of the proteins may be achieved by selective enzymatic or chemical cleavage from the M protein or by solid phase synthesis (see application of Fischetti mentioned under Related Applications). The proteins disclosed herein, whether from the gene expression of a modified virus or from other synthesis are not products of nature because the proteins herein are not the entire M protein, but are the same or substantially the same as an amino acid sequence in only a portion of the M protein; said portion comprising the conserved exposed region of the M protein (or a portion thereof).

Furthermore, the proteins disclosed herein do not have the same characteristics and utility as any M protein or other naturally occurring protein, because the M protein cannot be utilized to protect against streptococcal infections because of species variability of the M protein from different strains of streptococci, whereas the proteins herein can be used to prepare vaccines affording protection which is not strain specific. Thus, the proteins disclosed herein are not products of nature as they do not exist as distinct entities in nature and have never before been produced, and because no product of nature has the same properties as these proteins.

BRIEF DESCRIPTION OF DRAWINGS

FIG. 1 shows the complete amino acid sequence of the M6 protein from strain D471 of a group A streptococcal culture from The Rockefeller University collection.

FIG. 2 illustrates a model of the complete M6 protein from strain D471 as it exists on the cell wall.

DETAILED DESCRIPTION

Figure 2:
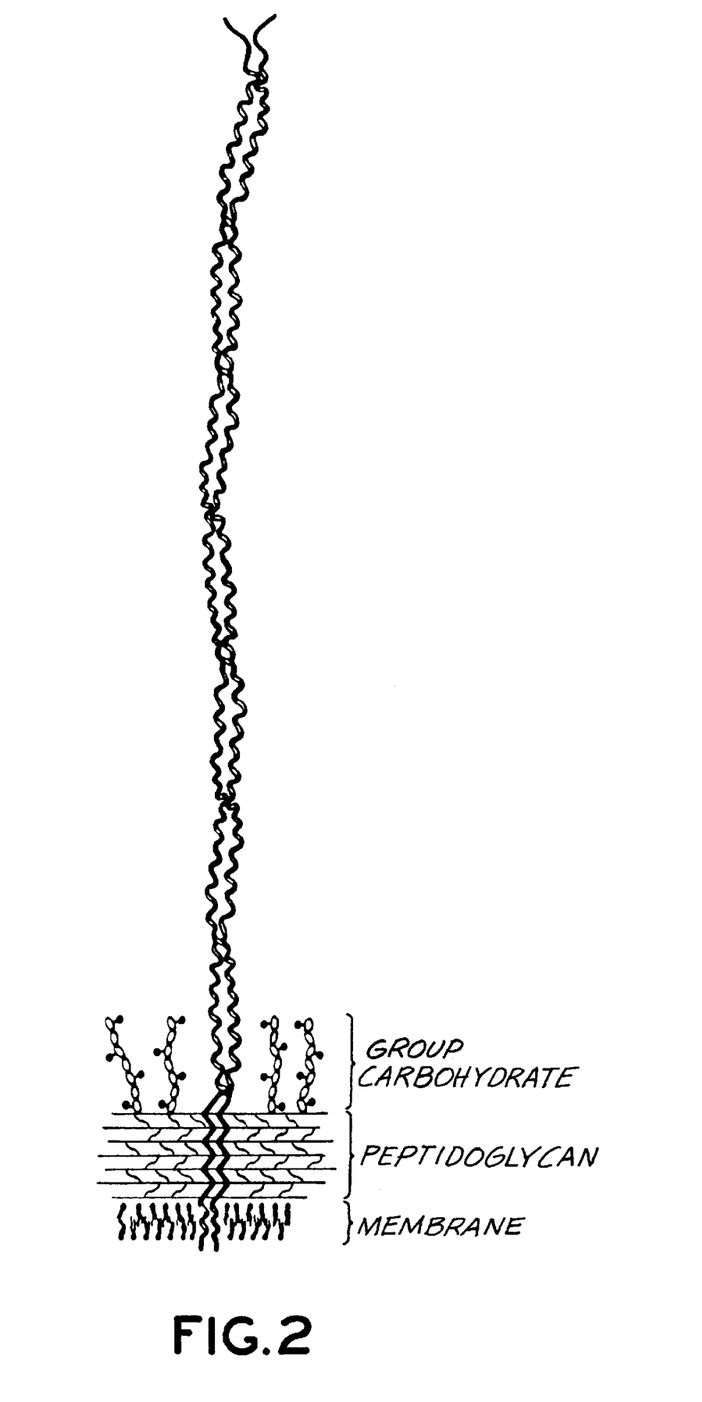

It will be seen from FIG. 2 that a portion of the M protein, the carboxy terminus, is embedded in the peptidoglycan of the cell wall, and in the cytoplasmic membrane. A segment of the M molecule is sheltered by the carbohydrate of the cell wall which is composed of a rhamnose backbone (open circle) and N-acetylglycosamine branches (closed circles). The distal amino terminus of the M-protein is non-helical. Most of the M-molecule between the carbohydrate shelter and the non-helical region is exposed on the surface of the streptococcus.

FIG. 1 is the complete amino acid sequence of an M protein from a specific strain. M proteins from other strains will have generally the same structural features and conformation, but the amino acid sequences will vary. The principal variations occur towards the amino terminal. The molecules become more and more conserved towards the carboxy end. Thus homology within M molecules of different serotypes progressively increases at sites which are closer to the carboxy terminus and more proximal to the cell wall. The conserved exposed region runs from about position 170 to position 299, and is more generally regarded as the region starting from Ile at position 210. The conserved exposed region is preferably from about position 210 to approximately position 298. The balance of the molecule is considered to be the conserved nonexposed region. This invention is concerned with the conserved exposed region of the M-protein molecule.

It is the variability at the amino terminus which is responsible for the antigenic variation of the M protein. Type specific antibodies which afford protection against one serotype are not effective to resist infection by other serotypes in an opsonophagocytosis assay. Thus, it is theoretically possible for an individual to be infected many times with different streptococcal strains, and each infection will continue until the immune system has generated antibodies directed to the type specific N-terminal region of the M-molecule.

Figure 7:
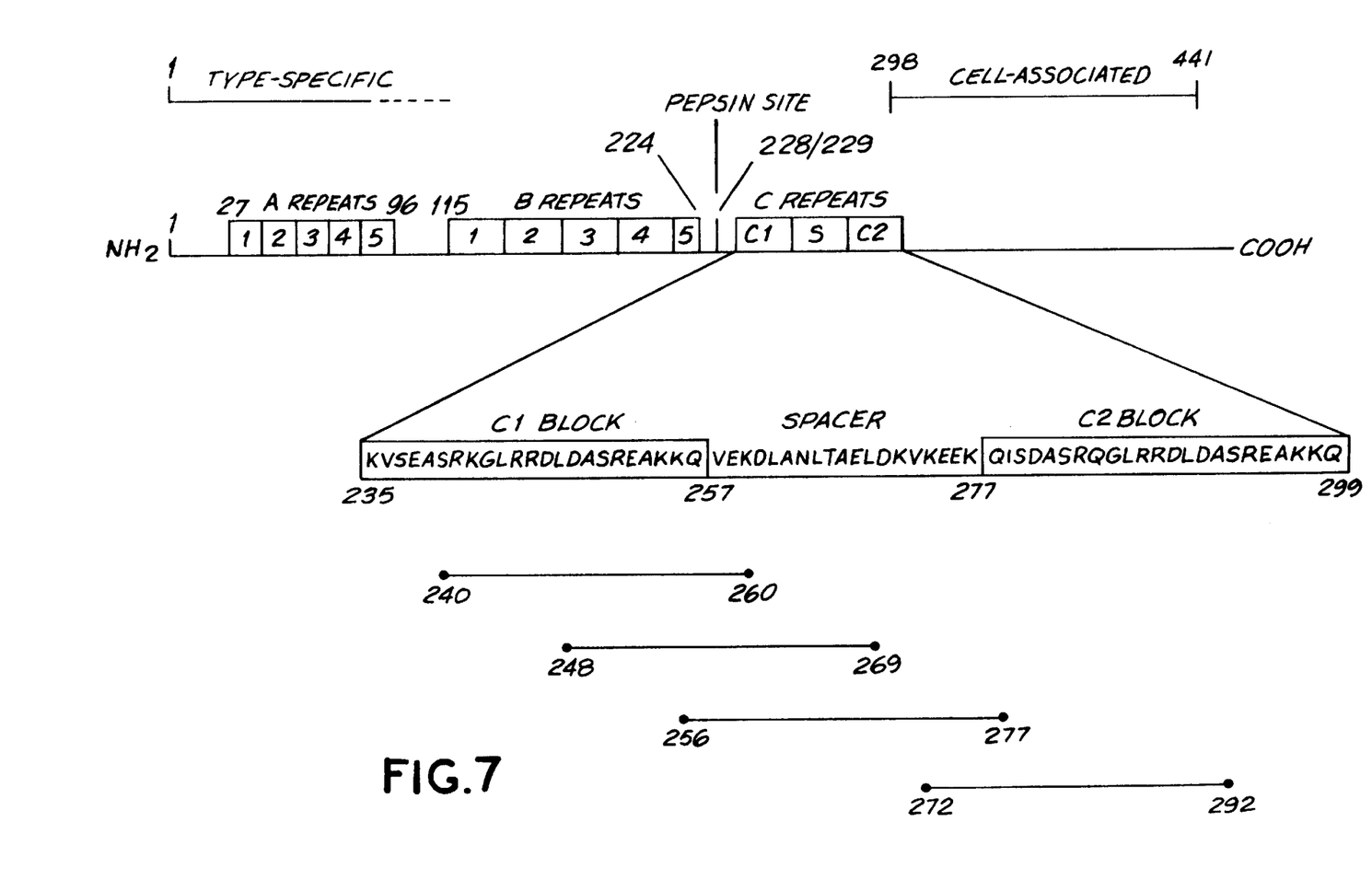
FIG. 7 illustrates the location of the preferred conserved region peptides.

It is believed that the C repeat region of the M protein consists of highly conserved C repeat blocks, interspersed by spacer sequences which may be less highly conserved among different serotypes (see FIG. 7). The highly conserved C1 and C2 repeat blocks are located adjacent to the cell wall, e.g., in type 6 streptococci.

In particular, FIG. 7 shows that the amino end of M protein is type specific (antigenically variable). Sequences in position 298–441 are generally cell associated. Within the conserved region occurs the C repeat region composed of the C1 Block, Spacer and C2 Block. The non-type-specific epitopes of M6 which are shared among other M protein serotypes to varying degrees are located here. Monoclonal and affinity-purified antipeptide antibodies which map to the B repeat region and pepsin site of M6 protein are shared among only 10% to 17% of more than 50 distinct serotypes. In contrast, antibodies which map to the adjacent C repeat region are shared among approximately 60% to 70% of the serotypes. While proteins of this invention can extend from the B5 repeat Block through the C repeat region and even from the B4 repeat Block to the carboxy terminus, for broad-based protection, it is preferred that the protein be the same or substantially similar to the conserved exposed region which runs from about position 170 to position 299, and it is even more preferred that the proteins be the same or substantially similar to the region that runs from about position 235 to position 299; i.e., completely contained within the highly conserved C repeat region. In the following discussion, numerals in parenthesis following the word peptide or protein or polypeptide, or the like, such as "peptide (240–260)" refer to a peptide or protein or polypeptide having an amino acid sequence which is the same or substantially the same as the sequence in the M6 protein spanning from the position of the first numeral to the position of the second numeral.

Absorption assays with antipeptide Fabs, indicate that one Class I-specific mAb (10B6) maps to peptide (240–260), whereas the other Class I-specific mAb (10F5) maps to both peptide (240–260) and peptide (272–292). In addition, antipeptide antibodies directed to peptide (240–260) and peptide (272–292) have substantial immunoreactivity with the extracted forms of several Class II M proteins on Western blot, although antipeptide antibodies to peptide (248–269) and peptide (256–277) may be Class I-specific. Thus, within a narrow region of the C repeat region of M6 protein, there may be both Class I-specific and shared antigenic determinants. Therefore, a vaccine consisting of antigens corresponding to the C repeat region will protect against both Class I and Class II streptococci.

Thus, in addition to proteins which are the same or substantially the same as the sequence of the conserved exposed region of the M6 protein, there is a preference for proteins which are the same as or are substantially similar to the sequence of the C repeat region or a portion thereof. Similarly preferred proteins include polypeptide (216–235), polypeptide (248–269), polypeptide (275–284), polypeptide (240–260), polypeptide (256–277), and polypeptide (272–292) (see application of Fischetti mentioned under Related Applications).

Vaccines for use to protect against streptococcal infection have been proposed previously. These vaccines have been prepared from polypeptides from the hypervariable amino end of the molecule. They have enjoyed some success in providing type specific immunity against homologous serotypes. Their performance has been improved by incorporating several type specific determinants in the same multivalent vaccine. However, given the enormous array of existing M serotypes, this procedure is not an attractive one.

Group A streptococci are widespread human pathogens which are responsible for nasopharyngeal infections and impetigo. There are approximately 30 million cases of group A streptococcal infections each year in the United States alone. Despite the fact that streptococcal infection can be successfully treated with antibiotics, in the interim it often causes significant discomfort and loss in productivity. A small percentage of infected individuals afflicted with streptococcal infection develop a more serious illness such as rheumatic fever and glomerulonephritis. In developing countries, rheumatic fever is the leading cause of heart disease among children. Thus, there is a strong impetus to develop a safe and effective vaccine against group A streptococci.

Experience shows that streptococcal infections, particularly pharengytis are generally limited to children. The incidence of infection peaks at ages 6–8. Adults are apparently more resistant to such infections, presumably because they have built up an immunity which is effective against most serotypes. Hence, there may be an immunological response to streptococcal infections which produces antibodies which recognize epitopes on most, if not all streptococcal serotypes. It has been found that such epitopes are in the conserved region of the M protein which is not protected by its proximity to the cell wall, i.e., the conserved exposed region of the M protein.

While the identity of the amino acids in this region varies somewhat amongst serotypes, it generally runs from about amino acid 170 to position 299 on the M protein molecule, preferably from position 210 to 298 or 299 and even more preferably from about position 235 to about position 299.

Polypeptides or proteins from that region are capable of eliciting and do elicit a protective immune response when administered to a mammal in need of protection against streptococcal infection.

As is known, the mammalian body has several methods for protecting itself against infection by microorganisms. One is the adaptive system in which the immune response to an invading organism results in the production of IgG antibodies which function by allowing opsonization and phagocytosis mediated by complement. Another is the production or activation of IgA which is the predominant immunoglogulin of seromucous secretions such as saliva, tracheobronchial secretions, colostrum, milk and genitourinary secretions. IgG is also found in these secretions, but in a lesesr concentration. Secretory IgA (sIgA) is a dimeric form of IgA protected from proteolysis by the secretory component. One function of IgA is to prevent infective microorganisms from adhering, colonizing and invading the mucous tissue.

A presently preferred procedure for the practice of this invention involves, principally, the stimulation of the secretory immune system, particularly sIgA by intranasal or oral administration. There may be concomitant production of IgG, and both may contribute to the immunization. The invention will be described principally as applied to that procedure. The polypeptides of the invention may also be used to stimulate IgA as the principal response by parenteral administration with concomitant production of low level IgA.

Vaccinia virus and fowlpox virus are members of the family poxviridae. Within the family poxviridae is the genus orthopoxvirus and the genus avipoxvirus, inter alia. There are more than 20 viruses in the family poxviridae including viruses responsible for smallpox, cowpox, fowlpox and mammalian diseases.

Fowlpox is in the genus Avipoxvirus, whereas vaccinia and smallpox are in the genus Orthopoxvirus. The genus Avipoxvirus also includes canary pox, junco pox, pigeon pox, sparrow pox, starling pox and turkey pox. Characteristics of poxviruses include that the virons are large, brick-shaped (or ovoid in the case of the genus Parapoxvirus), approximately 300–450 by 170–260 nm in size, with an external envelope, a coat of tubular structures, and an internal structure made up of a DNA-containing core and one or two lateral bodies. The genome consists of a single molecule of dsDNA with covalently closed ends ("hairpins") with a size of 130–280 kbp. The viruses have more than 100 proteins and several enzymes (including a DNA-dependent RNA polymerase, guanylmethyltransferase and poly (A) polymerase). Initial transcription occurs within the virus core, leading to the synthesis of early proteins, some of which lead to uncoating of viral DNA allowing further transcription and DNA replication. Replication and assembly occur in the cytoplasm in viroplasm ("viral factories"), and virions are released by budding (extracellular enveloped virions) or by cell destruction (intracellular enveloped virions). There is a common poxvirus group antigen (nucleoprotein antigen), and member viruses of the genux Orthopoxvirus produce a nonvirion hemagglutinin.

This invention will be described principally as it relates to vaccinia and fowlpox as the vector for the gene expressing the conserved, exposed region of the M protein, but other vectors (viruses, especially members of poxviridae) can also be employed. Likewise, other genes for antigens of prokaryotes which are responsible for the virulence of said prokaryotes can also be employed. Fowlpox is a preferred vector because about 1 in 100,000 persons exposed to vaccinia have an adverse reaction (e.g., encephalitis) whereas no such reaction is known to occur from exposure to fowlpox. In addition, the natural host range of fowlpox virus is limited to avian species (see Taylor et al, "Protective immunity against avian influenza induced by fowlpox virus recombinant," Vaccine, vol. 6, December 1988, p. 504, incorporated herein by reference). The fowlpox strain designated herein FP-1 is a Duvette Strain modified to be used as a vaccine in day old chickens; the strain is a commercial strain designated O DCEP 25/CE67/2309 October 1980 and is available from Institute Merieux, Inc.

Vaccinia and fowlpox are eukaryotic viruses which complete most phases of their respective reproductive cycles within the cytoplasm of a host cell. They are non-transforming viruses, i.e., the viral DNA does not become integrated in the host genome nor do any viral gene products cause transformation. The viruses are considered to be non-oncogenic. Vaccinia has been used for approximately 200 years in vaccines for inoculation against smallpox and the medical profession is well acquainted with the properties of the virus when used in a vaccine. Although inoculation with vaccinia is not without risk, the risks are on the whole well known, well defined, and the virus is considered relatively benign.

Paoletti et al in U.S. Pat. Nos. 4,603,112, 4,722,848 and 4,769,330 have described procedures for the production of vaccinia strains in which the vaccinia genome has been modified, for example by introduction of a gene which is not naturally present. The procedures of these patents are generally applicable to the preparation of the products of this invention. And, each of U.S. Pat. Nos. 4,603,112, 4,722,848, and 4,769,330 are hereby incorporated herein by reference. In WO89/03429, published Apr. 20, 1989 (PCT/US88/02816, priority applications U.S. applications Ser. Nos. 090,711, 110,335, 186,054 and 234,390, respectively filed on Aug. 27, 1987, Oct. 20, 1987, Apr. 25, 1988, and Aug. 23, 1989), hereby incorporated herein by reference, Paoletti sets forth procedures for the production of fowlpox strains in which the fowlpox genome has been modified, for example, by introduction of a gene which is not naturally present. However, neither this publication nor the aforementioned Paoletti patents teaches or suggests introducing into a virus, especially vaccinia or fowlpox, a gene for a surface antigen (or portion thereof) of a prokaryote which is responsible for the virulence of said prokaryote; and, in particular, the aforementioned Paoletti publication and patents fail to teach or suggest introducing a gene for the conserved exposed region of the M protein (or for a portion thereof) into a virus, especially a vaccinia virus or a fowlpox virus. Furthermore, Paoletti in WO89/03429 fails to provide any practical utility for the insertion of prokaryotic DNA into a virus: Paoletti's only use of prokaryotic DNA is of the LacZ gene which expresses Beta-galactosidase in virtually any system and is commonly employed as a mere color marker. The expression of Beta-galactosidase by the insertion of the LacZ gene into a virus is not a teaching or suggestion of causing a virus to express an antigen (or portion thereof) which is responsible for the virulence of a prokaryote by the insertion into said virus of prokaryotic DNA for said antigen (or portion thereof).

It has now been discovered that a modified virus, preferably fowlpox virus or vaccinia virus, containing in their genome a genetically engineered gene expressing an antigen responsible for the virulence of a prokaryote, preferably the M6' gene or a gene expressing the conserved, exposed region of the M6 protein (M6' protein) can be employed successfully to generate an immune response in a mammalian host which is sufficient to protect the host against infections caused by said prokaryote, e.g., streptococcal infections such as streptococcal pharangytis.

Figure 3:
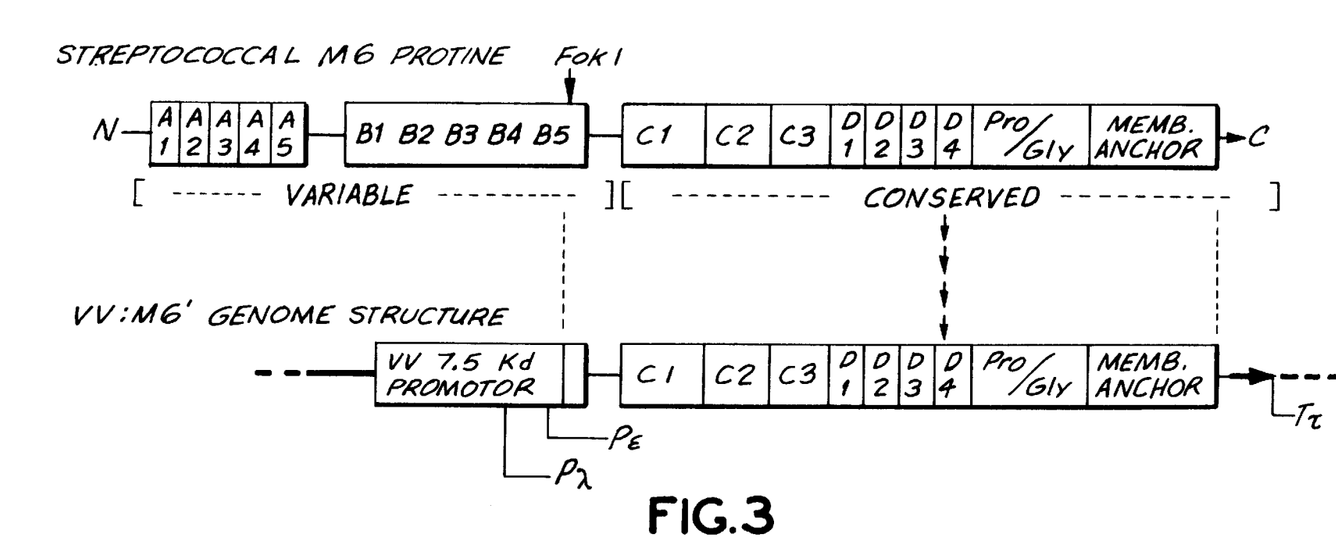
FIGS. 3 and 4 show the strategy utilized to produce products of this invention.
Figure 4:
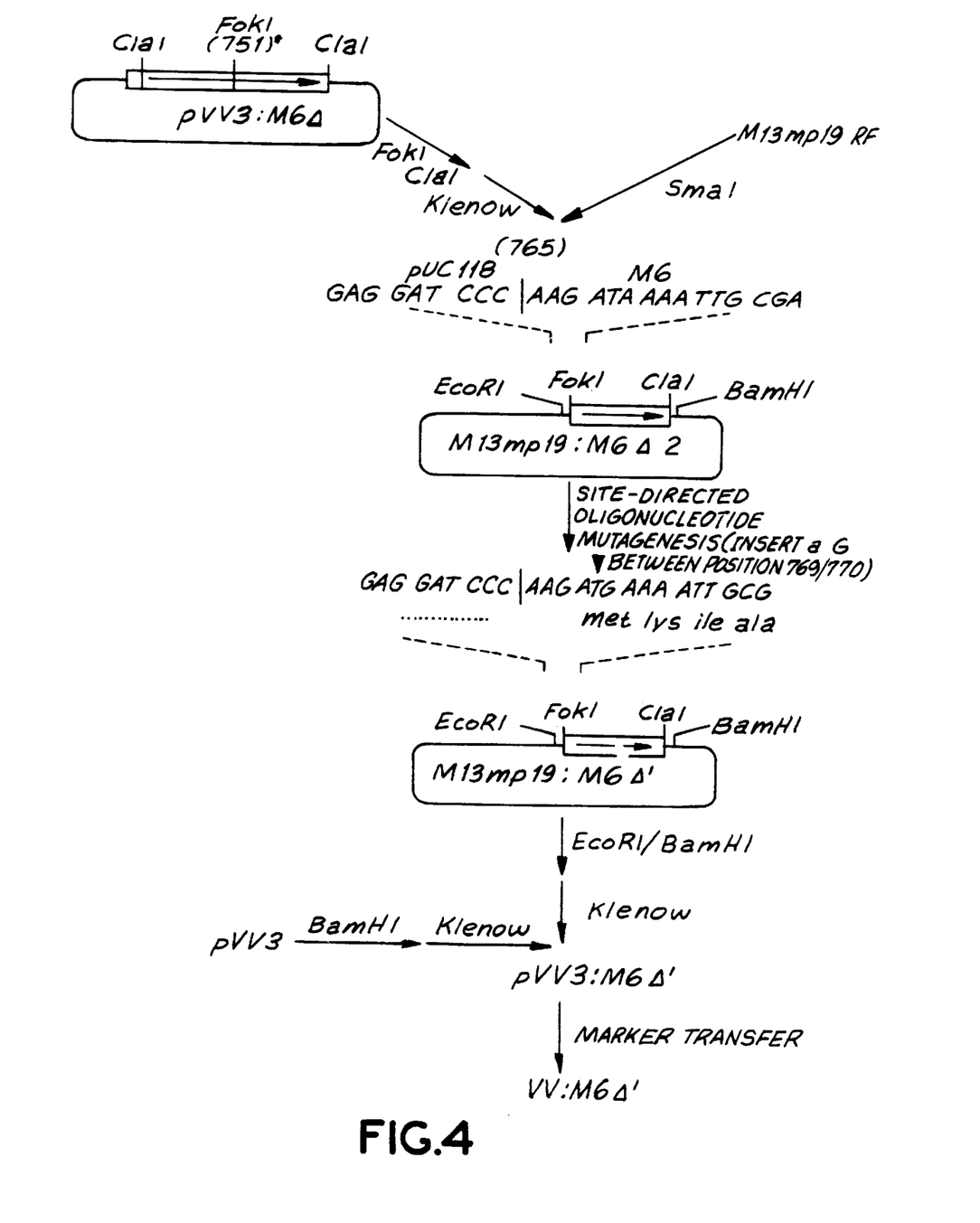

The strategy used to assemble and isolate an appropriate virus recombinant containing the M6' gene and expressing the M6' protein is shown in FIGS. 3 and 4. The production of the novel virus utilizes the known plasmid pVV3:M6 prepared as described by Hruby et al in Proc. Natl. Acad. Sci. USA Vol. 85 pp 5714–5717, August 1988 Microbiology (incorporated herein by reference) to produce the novel plasmid pVV3:M6' which is used to introduce the chimaeric M6' gene into the vaccinia or preferably the fowlpox virus genome to produce the recombinant virus VV:M6' or FPV:M6'.

It has been found that the novel vaccinia or fowlpox viruses containing the complete conserved region gene fragment of the M6 protein, i.e., containing the M6' gene for expressing a truncated M6 protein, herein identified as the M6' protein, will confer significant protection from bacterial mucosal colonization when us ed as a prophylactic vaccine. For convenience the novel vaccinia virus will be referred to herein as the VV:M6' virus; and the novel fowlpox virus will be referred to herein as the FPV:M6' virus.

The following non-limiting Examples are given by way of illustration only and are not to be considered a limitation of this invention, many apparent variations of which are possible without departing from the spirit or scope thereof.

EXAMPLES

Example 1

Virus Assembly (VV:M6')

FIG. 3 shows the structure of the VV:M6' recombinant virus. The top portion of the figure is a schematic representation of the major structural features of the protein encoded by the M6 open reading frame with conserved and variable regions among different M serotypes indicated. See Hollingshead et al, J. Biol. Chem. 261, 1677 (1986). The A, B, C, and D amino acid repeat blocks are indicated, as are the proline-glycine (Pro/Gly) rich region and the membrane anchor (M anchor). Using the indicated FokI site, the conserved 3'-half of the M6 gene was subdoned into a plasmid vector as described below. The genomic structure of the VV:M6' recombinant is shown at the bottom of the figure. The M6' insert is abutted to the constitutive 7.6 kDa viral thymidine kinase gene (bold arrows). The approximate location of early ($P_{68}$) and late ($P_{65}$) transcriptional start sites are indicated, as well as the site used for termination of early transcripts ($T_{96}$). The structure of the VV:M6' recombinant, the sequence of the junction regions, and the expression of the chimeric transcriptional unit was verified by DNA sequencing, Northern blot hybridization, and nuclease S1 mapping procedures.

In the first step for the construction of VV:M6', as shown in FIG. 4, the pVV:M6 plasmid was cut with FokI (cleaves at position 751 of the M6 sequence) and ClaI (cleaves at the 3' end of the insert). The fragment corresponding to the 3'-half of the M6 gene was isolated, the recessed ends filled in using the Klenow fragment of DNA polymerase I, and the blunt-ended fragment cloned into the SmaI site of M13mp 19 RF DNA. A recombinant phage containing the insert in the correct orientation was identified by hybridization with a strand specific oligonucleotide probe. Single-stranded DNA was prepared and used as a substrate for oligonucleotide-directed site-specific mutagenesis designed to introduce a G between positions 769 and 770 of the insert. This alteration, which was verified by Sanger dideoxynucleotide sequencing procedures, resulted in the Lys-209 codon of the M6 open reading frame being converted to anin-frame AGT codon. The mutagenized insert (M6') was excised from the phage DNA using EcoRI and BamHI which cut at the 5' and 3' ends, respectively, of the M6' insert. The recessed ends were blunted with Klenow, and the fragment was blunt-end ligated into the BamHI site of the pVV3 insertion plasmid, which was also filled in with Klenow. Restriction map and nucleotide sequence procedures were employed to select a recombinant plasmid containing the M6' insert in the correct orientation with regard to the VV 7.5 kDa promotor element. This pVV3:M6 recombination plasmid was used to introduce the chimeric gene into the VV genome using standard marker transfer technology. The recombinant virus (VV:M6') was grown, purified, and then carefully analyzed to verify that the M6' insert was present, intact, and actively transcribed in virus-infected cells.

Figure 5:
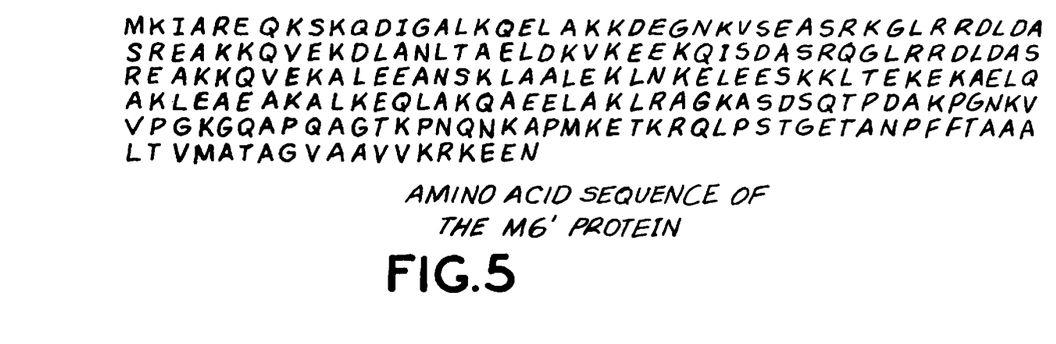
FIGS. 5 and 6 show the structure of the M6' protein and the M6' gene respectively.
Figure 6:
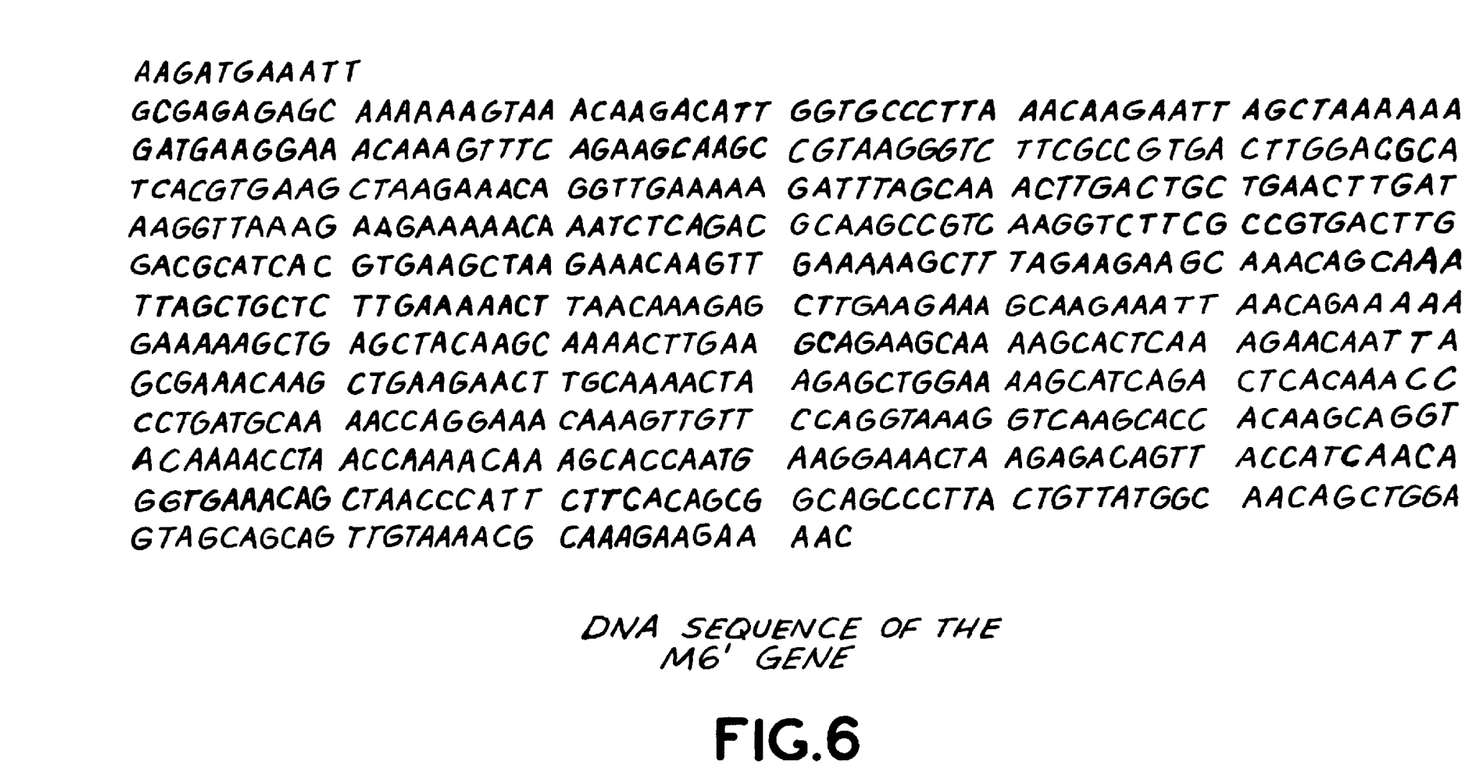

The structures of the M6' gene and the M6' protein are shown in FIGS. 5 and 6 using the standard symbols for the constituents.

Comparison of the amino acid sequence of the M6' protein (FIG. 5) to the full-length M6 protein (FIG. 1) reveals that the M6' protein includes the carboxy-terminal 234 amino acids of the M6 protein, from approximately amino acid 209 to the end of the molecule, and encompasses the conserved exposed region of the M6 protein.

Example 2

Virus Efficacy (VV:M6')

Groups of mice (Swiss CD1, Jackson Labs) were immunized intranasally with either the VV:M6' virus or the wild-type strain with a dose of $10^7$ to $10^8$ plaque forming units (PFU)/mouse. After four weeks, mice were challenged both intranasally and orally with M6 group A streptococci (strain S43/192 from the Rockefeller University Collection) which were made resistant to 200 ug/ml of streptomycin. All animals were housed 4-5/cage throughout the experiment. Preparation of the strain for challenge was as described by Bessen and Fischetti in Infect. Immun. 56,2666 (1988). Two separate challenges were performed using different doses of streptococci ($6\times10^6$ or $1\times10^7$ colony forming units (CFU/mouse). In each case, 20 ul of the streptococcal suspension were administered to each nostril and an additional 10 ul orally. Starting 24 hours after challenge, and at 24 to 72 hour intervals for ten days thereafter, throats were swabbed (Calgiswab type 4, Spectrum) and cultured on blood agar plates containing 200 ug/ml of streptomycin to both discriminate and prevent competition between the growth of input streptococci and normal flora organisms. Cultures were grown overnight at 37° C. and scored for the presence of Beta-hemolytic streptococci. Mice which had died after challenge were autopsied and their spleens aseptically removed and cultured on streptomycin to both discriminate and prevent competition between the growth of input streptococci and normal flora organisms. Cultures were grown overnight at 37° C. and scored for the presence of Beta-hemolytic streptococci. Mice which had died after challenge were autopsied and their spleens aseptically removed and cultured on streptomycin-containing blood agar.

The results of the study are shown in Table I.

TABLE I

THROAT CULTURES AFTER INTRANASAL AND ORAL CHALLENGE OF MICE VACCINATED INTRANASALLY WITH WILD-TYPE OR RECOMBINANT VACCINIA VIRUS

| | DAYS POST CHALLENGE | | | | | | | DAYS POST CHALLENGE | | | | | |
|---|---|---|---|---|---|---|---|---|---|---|---|---|---|
| MICE | 1 | 2 | 3 | 6 | 8 | 10 | MICE | 1 | 2 | 3 | 6 | 8 | 10 |
| | WILD-TYPE VV VACCINE: | | | | | | | RECOMBINANT VV:M6' VACCINE | | | | | |
| A. EXPERIMENT I[1] | | | | | | | | | | | | | |
| | CFU in throat culture[2] | | | | | | | CFU in throat culture | | | | | |
| 1 | >100 | >100 | >100 | * | | | 1 | 0 | 0 | >100 | * | | |
| 2 | >100 | >100 | >100 | * | | | 2 | 0 | 0 | * | | | |
| 3 | >100 | >100 | >100 | * | | | 3 | 0 | 0 | 1 | >100 | * | |
| 4 | >100 | 92 | >100 | * | | | 4 | 0 | 5 | 4 | 0 | 3 | 0 |
| 5 | 63 | >100 | >100 | * | | | 5 | 0 | 3 | 3 | 1 | 1 | 0 |
| 6 | 0 | 15 | * | | | | 6 | 0 | 9 | 0 | 0 | 0 | 0 |
| 7 | 43 | >100 | 82 | 3 | 4 | 0 | 7 | 0 | 1 | 0 | 0 | 0 | 0 |
| 8 | 35 | 1 | 17 | 2 | >100 | 20 | 8 | 0 | 0 | 0 | 1 | 0 | 0 |
| 9 | 1 | 1 | 1 | 2 | >100 | 5 | 9 | 0 | 0 | 0 | 0 | 0 | 0 |
| 10 | 0 | 0 | 0 | >100 | >100 | >100 | 10 | 0 | 0 | 0 | 0 | 0 | 0 |
| 11 | 0 | 0 | 0 | 0 | 65 | * | 11 | 0 | 0 | 0 | 0 | 0 | 0 |
| 12 | 3 | 8 | 1 | 0 | 1 | 0 | 12 | 0 | 0 | 0 | 0 | 0 | 0 |
| 13 | 0 | 0 | 88 | 0 | 0 | 1 | 13 | 0 | 0 | 0 | 0 | 0 | 0 |
| 14 | 1 | 7 | 0 | 0 | 0 | 0 | 14 | 0 | 0 | 0 | 0 | 0 | 0 |
| 15 | 4 | 0 | 0 | 0 | 2 | 0 | 15 | 0 | 0 | 0 | 0 | 0 | 0 |
| 16 | 0 | 0 | 2 | 0 | 0 | 0 | 16 | 0 | 0 | 0 | 0 | 0 | 0 |
| 17 | 0 | 0 | 0 | 0 | 0 | 0 | 17 | 0 | 0 | 0 | 0 | 0 | 0 |
| | | | | | | | 18 | 0 | 0 | 0 | 0 | 0 | 0 |
| | | | | | | | 19 | 0 | 0 | 0 | 0 | 0 | 0 |
| | | | | | | | 20 | 0 | 0 | 0 | 0 | 0 | 0 |
| B. EXPERIMENT II | | | | | | | | | | | | | |
| 1 | >100 | >100 | * | | | | 1 | >100 | >100 | * | | | |
| 2 | >100 | >100 | >100 | * | | | 2 | >100 | >100 | >100 | * | | |
| 3 | >100 | >100 | 13 | * | | | 3 | 14 | >100 | 0 | 50 | >100 | >100 |
| 4 | >100 | >100 | >100 | >100 | * | | 4 | 0 | 61 | 0 | 0 | 0 | 0 |
| 5 | 36 | 86 | 67 | * | | | 5 | 0 | 3 | 0 | 0 | 0 | 0 |
| 6 | >100 | >100 | 5 | >100 | >100 | >100 | 6 | 0 | 0 | 0 | 0 | 0 | 0 |
| 7 | >100 | 37 | 2 | >100 | >100 | >100 | 7 | 0 | 0 | 0 | 0 | 0 | 0 |
| 8 | 16 | 49 | 32 | >100 | 6 | 85 | 8 | 0 | 0 | 0 | 0 | 0 | 0 |

* = DEAD, After autopsy, spleens cultured on streptomycin-containing blood agar revealed β-hemolytic streptococci.
[1] Streptococcal challenge dose in Experiment I was 6 x 10⁶ 6 CFR and 1 x 10⁷ CFR in Experiment II.
[2] Colony forming units of β-hemolytic streptococci on streptomycin-containing blood agar of throat swabs from mice challenged with group A streptococci.

As will be seen, pharyngeal colonization of animals immunized with wild-type virus differed significantly from those immunized with the VV:M6' recombinant. Of the VV:M6' vaccinated animals in both dosage groups, only 16% of the 152 total swabs taken were positive with 10(6%) yielding >100 CFU, whereas 69% of the 115 swabs were positive in the wild-type group with 40(35%) displaying >100 CFU. On average, >70% of the animals immunized with wild-type virus were culture positive for group A streptococci at every swab day up to 10 days after challenge. This is compared to <30% colonization of mice immunized with the VV:M6' virus and cultured over the same time period after challenge. These figures are summarized in Table II.

TABLE II

SUMMARY OF THROAT CULTURE RESULTS OF MICE VACCINATED INTRANASALLY WITH EITHER WILD-TYPE OR RECOMBINANT VACCINIA VIRUS[1]

| | DAYS POST CHALLENGE[2] (Culture positive[3]/total challenged) [% colonized] | | | | | |
|---|---|---|---|---|---|---|
| VV VACCINE | | | | | | |
| Wild Type | 19/25 [76] | 18/25 [72] | 19/25 [76] | 18/25 [72] | 21/25 [84] | 19/25 [76] |
| Recombinant (VV:M6') | 3/28 [11] | 9/28 [32] | 7/28 [25] | 8/28 [29] | 8/28 [29] | 8/28 [29] |

1 Compiled from Table I
2 Significant difference (p>0.005) at all time points between wild-type and recombinant vaccinated mice according to chi-square analysis.
3 Animals culture positive for group A streptococci or dead after streptococcal challenge.

Table I shows the results of two separate experiments in which different groups of mice treated with either the wild type VV vaccine, or with VV:M6' vaccine and subsequently challenged. As will be seen, in the first group of 17, 65% of animals immunized with the wild-type virus were colonized on day 1 after streptococcal challenge and remained essentially so or died during the duration of the experiment. In the second group of 8, 100% of the mice were colonized on day 1, and more than half of them were dead by day 8. In the VV:M6' immunized mice, 0/20 (0%) in Experiment I and only 3/8 (38%) in Experiment II exhibited a positive throat culture on day 1 after challenge. Only 18% of all of the mice vaccinated with VV:M6' died during the experiments, whereas 48% of all of the mice vaccinated with wild type died. Spleen cultures taken from dead animals revealed Beta-hemolytic streptococci.

Kinetic ELISA, applied as described by Bessen and Fischetti, *Infect. Immun.*, 56,2666 (1988) and Fischetti et al *J. Immunol.* 141, 3592 (1988) (each of which incorporated herein by reference) was utilized to confirm the presence of antibodies. At the time of streptococcal challenge (4 weeks post immunization) M protein specific IgG was significantly elevated in the serum of VV:M6' vaccinated animals and absent from those animals which received wild-type virus, Comparable high levels of antibodies to vaccinia virus was observed in both wild-type and VV:M6' immunized animals.

Example 3

Virus Assembly (FPV:M6')

The insertion plasmid pVV3:M6' containing the M6' gene is produced as set forth in Example 1, and is inserted at a non-essential site in the genome of an attenuated fowlpox virus (FPV) (FP-1 strain). The gene is inserted between two HincII sites of a 900 bp PvuII fragment of the FP-1 genome with subsequent deletion of approximately 30 bp. The recombinant fowlpox virus, FPV:M6' is produced by methods described above in Example 1 for the vaccinia virus. Other previously described methods for the fowlpox virus and for the vaccinia virus respectively, such as in Taylor et al, supra, or as in Panicali et alr "Construction of poxviruses as cloning vectors: Protective insertion of the thymidine kinase gene grom herpes simplex virus into the DNA of infectious vaccinia virus," Proc. Natl Acad. Sci. USA 1982, 79, 4927, incorporated herein by reference, can also be employed to produce the insertion plasmid and the recombinant fowlpox virus. The structure of the FPV:M6' recombinant, the sequence of the junction regions, and the expression of the chimeric transcriptional unit are verified by DNA sequencing, Northern blot hybridization, and nuclease S1 mapping procedures. The recombinant virus (FPV:M6') is grown, purified and then carefully analyzed to verify that the M6' insert is present, intact and actively transcribed in virus-infected cells.

The structures of the M6' gene and the M6' protein are shown in FIGS. 5 and 6 using standard symbols for constituents.

Example 4

Virus Efficacy (FPV:M6')

Groups of mice are immunized with either FPV:M6' virus or the wild-type strain and are thereafter challenged with M6 group A streptococci in accordance with the procedures set forth in Example 2. Likewise, confirmation of the presence of antibodies is as set forth in Example 2. The results obtained are substantially the same as set forth in Example 2.

The results of the preceeding Examples clearly show the ability of the recombinant vaccinia virus and of the recombinant fowlpox virus of this invention to express sufficient quantities of M6' protein to induce an immune response to protect against streptococcal colonization in mammals.

Novel products which have thus far been described include the M6' gene, the plasmid pVV3:M6' containing the M6' gene, the M6' protein and the recombinant viruses VV:M6' and FPV:M6'. Without any admission of the need to do so, it is stated that a sample of the pVV3:M6' plasmid in *E. coli* has been deposited at the American Type Culture Collection under the accession number 68003; and, a sample of the recombinant vaccinia virus VV:M6' has also been deposited under the accession number ATCC VR 2242.

Those skilled in the art will recognize that, while the invention has been described by reference to specific products, it is not limited to these specific products. The concept of the invention can be practiced utilizing products that have similar activities, and there may be produced by chemical synthesis, genetic engineering or other techniques. For example, the M6' gene can be modified by addition or deletion of one or several codons, and the resulting modified M6' gene will, when incorporated into a virus such as a vaccinia virus or a fowlpox virus to give rise to the expression of modified M6' proteins having the same or substantially the same protective capacity for mammals against bacterial infection. Although this disclosure speaks of a "conserved exposed region" it will be understood that not every such region found in every streptococcal strain will in fact be identical, nor will the genes that produce them be identical. They will however all have substantially the same activity, i.e., the gene will produce a protein of the same general region of the M-protein and the protein will afford protection against streptococcal infection. All such modifications of the novel products of this invention are included within its scope.

The vaccines of this invention will be prepared, typically for nasal, oral or parenteral administration, in accordance with standard techniques well known to those skilled in the pharmaceutical arts. Examples of such compositions include solid compositions for oral administration such as capsules, tablets, pills, and the like; liquid preparations for oral administration suspensions, syrups or elixers and preparations for parenteral administration such as sterile suspension or emulsions. Many of these compositions can be adopted for nasal administration utilizing a type of packaging from which the composition can be delivered by the application of air, or other gas, pressure. They may also be manufactured in the form of sterile solid compositions which can be suspended in sterile water, physiological saline or glucose.

All such compositions will contain a sufficient amount of modified vaccinia virus and/or fowlpox virus to generate a protective response in the host or some other injectable, oral or nasal medium just prior to use.

The product can be provided in lyophilized form for reconstituting in isotonic aqueous, saline buffer.

Optimal dosages and regiments for a given mammalian host can be readily ascertained by those skilled in the art. Many factors well known to physicians and veterinarians will be taken into account principally including age and weight as well as route of administration. Booster techniques such as employed with other vaccines may be employed.

Having thus described in detail the preferred embodiments of the present invention, it is to be understood that the invention defined by the appended claims is not to be limited by particular details set forth in the above description as many apparent variations thereof are possible without departing from the spirit or scope of the present invention.

What is claimed is:

1. The M6' gene.

2. A virus comprising the M6' gene of claim 1, wherein said virus is selected from the group consisting of vaccina virus and fowlpox virus.

3. The pVV3:M6' plasmid.

4. A gene encoding a protein, wherein said protein consists of an amino acid sequenice selected from the group consisting of the amino acid sequence of the conserved region of the M6 protein;

the M6' protein;

peptide (170–299);

peptide (210–299);

peptide (210–298);

peptide (216–235);

peptide (235–299);

peptide (235–257);

peptide (240–260);

peptide (248–269);

peptide (256–277);

peptide (258–276);

peptide (275–284);

peptide (272–292); and peptide (277–299).

5. A plasmid comprising a gene according to claim 4.

6. A virus containing a gene according to claim 4, wherein said virus is selected from the group consisting of vaccina virus and fowlpox virus.

7. A DNA molecule comprising a gene according to claim 4 operably linked to a heterologous DNA.

8. A DNA molecule encoding a protein consisting of up to 234 contiguous amino acids from the full-length M6 protein, wherein said contiguous amino acids are selected from the group consisting of the conserved region of the M6 protein;

the M6' protein;

peptide (170–299);

peptide (210–299);

peptide (210–298);

peptide (216–235);

peptide (235–299);

peptide (235–257);

peptide (240–260);

peptide (248–269);

peptide (256–277);

peptide (258–276);

peptide (275–284);

peptide (272–292); and peptide (277–299).

9. A plasmid comprising a DNA molecule according to claim 8.

10. A virus containing a DNA molecule according to claim 8, wherein said virus is selected from the group consisting of vaccina virus and fowlpox virus.

11. A DNA molecule comprising a DNA molecule according to claim 8 operably linked to a heterologous DNA.

* * * * *